United States Patent
Lueken et al.

(10) Patent No.: US 8,138,379 B2
(45) Date of Patent: Mar. 20, 2012

(54) ONE-STAGE CONTINUOUS PROCESS FOR HYDROFORMYLATING HIGHER OLEFINS OR OLEFIN MIXTURES

(75) Inventors: Hans-Gerd Lueken, Marl (DE); Stefan Drees, Duelmen (DE); Alfred Kaizik, Marl (DE); Wilfried Bueschken, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 115 days.

(21) Appl. No.: 12/738,111

(22) PCT Filed: Oct. 28, 2008

(86) PCT No.: PCT/EP2008/064584
§ 371 (c)(1),
(2), (4) Date: Apr. 15, 2010

(87) PCT Pub. No.: WO2009/080396
PCT Pub. Date: Jul. 2, 2009

(65) Prior Publication Data
US 2010/0249464 A1      Sep. 30, 2010

(30) Foreign Application Priority Data
Dec. 20, 2007  (DE) .......................... 10 2007 061 649

(51) Int. Cl.
C07C 45/50      (2006.01)
C07C 29/14      (2006.01)
(52) U.S. Cl. ...................................... 568/451; 568/880
(58) Field of Classification Search .................. 568/451, 568/880
See application file for complete search history.

(56) References Cited

U.S. PATENT DOCUMENTS

| | | | |
|---|---|---|---|
| 6,015,928 | A | 1/2000 | Gubisch et al. |
| 6,720,457 | B2 | 4/2004 | Drees et al. |
| 6,723,884 | B1 | 4/2004 | Grenacher et al. |
| 6,960,699 | B2 | 11/2005 | Toetsch et al. |
| 7,179,947 | B2 | 2/2007 | Lueken et al. |

FOREIGN PATENT DOCUMENTS

| | | |
|---|---|---|
| DE | 199 39 491 | 2/2001 |
| EP | 0 850 905 | 7/1998 |

OTHER PUBLICATIONS

U.S. Appl. No. 12/682,500, filed Apr. 9, 2010, Lueken, et al.

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to a one-stage continuous process for hydroformylating olefins having at least 5 carbon atoms to the corresponding aldehydes and/or alcohols having at least 6 carbon atoms in the presence of unmodified cobalt catalysts in a process in which, in the presence of an aqueous phase and of an organic phase, catalyst formation, catalyst extraction and hydroformylation proceed in the same reactor, which is characterized in that more aqueous cobalt salt solution is fed into the reactor as an aqueous phase with the liquid reaction mixture and is discharged from the reactor with the gas phase, and in that the level of the aqueous bottom phase is kept constant by continuously conducting a portion of the aqueous bottom phase out of the reactor.

13 Claims, 3 Drawing Sheets

Figure 1:
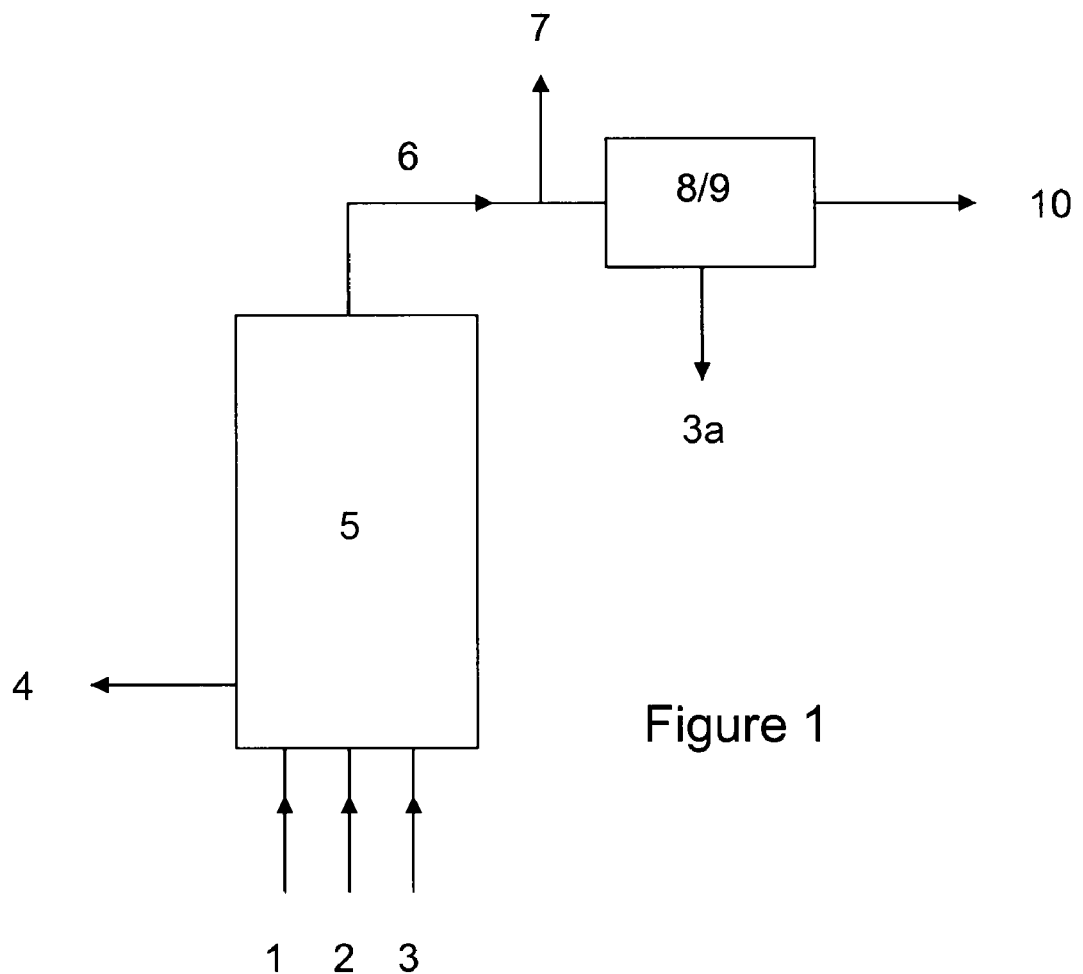

ONE-STAGE CONTINUOUS PROCESS FOR HYDROFORMYLATING HIGHER OLEFINS OR OLEFIN MIXTURES

The present invention relates to a single-stage continuous process for the hydroformylation of higher olefins or olefin mixtures in the presence of unmodified cobalt catalysts, by means of which higher oxo aldehydes and/or alcohols can be obtained.

It is known that higher alcohols, in particular ones having from 6 to 25 carbon atoms, can be obtained by catalytic hydroformylation (oxo process) of the olefins having one less carbon atom and subsequent catalytic hydrogenation of the aldehyde- and alcohol-containing reaction mixtures. They are used predominantly for the preparation of plasticizers and detergents. However, it is also possible to separate off aldehydes from the hydroformylation mixtures by distillation. These can be utilized, for example, for the preparation of carboxylic acids.

The type of catalyst systems and the optimal reaction conditions for the hydroformylation depend on the reactivity of the olefin used. The dependence of the reactivity of olefins on this structure is described, for example, by J. Falbe, New Syntheses with Carbon Monoxide, Springer-Verlag, Berlin, Heidelberg, New York, 1980, page 95 ff. The differing reactivity of, in particular, the isomeric octenes is likewise known (B. L. Haymore, A. van Hassett, R. Beck, Annals of the New York Acad. Sci., 415 (1983), pages 159-175).

Industrial olefin mixtures which are used as starting materials for the oxo process contain olefin isomers of various structures having different degrees of branching, different positions of the double bond in the molecule and possibly also different numbers of carbon atoms. This applies particularly to olefin mixtures which have been formed by dimerization or trimerization or further oligomerization of $C_2$-$C_5$-olefins or other readily available higher olefins or by cooligomerization of the olefins mentioned. As examples of typical isomeric olefin mixtures which can be converted by rhodium-catalyzed or preferably cobalt-catalyzed hydroformylation into the corresponding aldehyde and alcohol mixtures, mention may be made of tripropenes and tetrapropenes and also dibutenes, tributenes and tetrabutenes.

If alcohols having a very low degree of branching are sought as hydroformylation product, the hydroformylation is advantageously carried out using unmodified cobalt catalysts. Compared to rhodium catalysts, cobalt catalysts give, proceeding from an identical olefin mixture, higher yields of the particularly valuable straight-chain oxo products.

The hydroformylation of olefins using unmodified cobalt catalysts can, leaving aside the catalyst work-up, be carried out in one or more stages.

The known multistage processes for preparing oxo aldehydes in the presence of unmodified cobalt catalysts have a number of technical disadvantages. Thus, two technically complicated process steps, namely precarbonylation and catalyst extraction, are necessary to prepare the cobalt catalyst required for the hydroformylation. Due to the mass transfer processes occurring in the two process steps, namely gas/liquid mass transfer in the precarbonylation and liquid/liquid mass transfer in the catalyst extraction, two separate pressure-rated apparatuses, for example stirred vessels or packed columns, are required. The actual hydroformylation takes place subsequently in a separate reactor, once again a pressure reactor.

The German patent application DE 196 54 340 describes a process in which precarbonylation, catalyst extraction and olefin hydroformylation are carried out in one reactor. Compared to the known multistage processes, this process has the advantages of a lower capital outlay and lower operating costs. However, it has the disadvantage that carrying out the single-stage process is quite difficult since the process substeps such as catalyst formation, extraction of the catalyst into the organic phase and hydroformylation occur simultaneously. An aqueous cobalt salt solution in which the catalyst is formed is present in the lower part of the reactor. The hydroformylation takes place mainly in the homogeneous organic phase. The hydroformylation mixture leaving the reactor and the synthesis gas taken off continuously carry water and cobalt compounds from the reactor, so that further cobalt compounds and water have to be fed in continually.

Hydridotetracarbonylcobalt and hydridotetracarbonyldicobalt and other cobalt compounds having an oxidation number of less than 2 present in the hydroformylation product of this process are oxidized to cobalt(II) salts by means of oxygen in the presence of an aqueous cobalt(II) salt solution. The aqueous cobalt salt solution is separated from the organic phase and part of it is fed as catalyst precursor into the hydroformylation reactor. The aqueous phase contains mainly cobalt formate because formic acid is formed in the process, either directly from carbon monoxide and water or by hydrolysis of alkyl formats formed as by-products.

The content of cobalt compounds in the acidic (with formic acid) aqueous phase (pH=1-4) is thus determined largely by the solubility of cobalt formate. The content of cobalt compounds, calculated as elemental cobalt, can be up to about 1.7% by mass.

Furthermore, the amount of cobalt introduced into the reactor depends on the mass of the cobalt salt solution. In processes in which catalyst formation, catalyst extraction and hydroformylation are carried out simultaneously in the same reactor, as described, for instance, in DE 196 54 340, only a certain amount of cobalt salt solution can be fed in while keeping the aqueous bottom phase constant. The amount of aqueous cobalt salt solution fed in is just enough for the amount of water present therein to correspond exactly to the amount of water discharged with the liquid reaction mixture and the gas from the reactor.

The two abovementioned boundary conditions result in the following disadvantages: In the hydroformylation of olefins or olefin mixtures having intermediate or high numbers of carbon atoms (more than eight carbon atoms), the amount of cobalt(II) salt converted into the active catalyst until a pseudo-steady-state equilibrium is established under customary hydroformylation conditions (temperatures above 160° C. and operating pressures above 200 bar), is, based on the cobalt salt solution fed in, proportionately greater than that transported out of the reactor as water with the liquid organic phase and the gas. This means that the cobalt concentration in the aqueous phase in the reactor becomes lower than in the solution fed in. At temperatures at which the rate of formation of the catalyst is relatively low, this concentration effect is tolerable. If the rate constant for formation of the catalyst is increased by raising the temperature in order to obtain a more active catalyst, the decrease in the concentration of cobalt salts in the aqueous phase inhibits catalyst formation.

In the hydroformylation of higher olefins or olefin mixtures which themselves or their hydroformylation products dissolve little if any water, only a small amount of cobalt salts can be introduced into the reactor because of the water balance. The amount of active catalyst and thus the olefin conversion are correspondingly low. In the limiting case, when no water is carried from the reactor with the organic phase and gas, a continuous process, for instance as described in DE 196 54 340, cannot be carried out.

It is therefore an object of the invention to improve the single-stage hydroformylation process comprising catalyst formation, catalyst extraction and hydroformylation in the same reactor in such a way that the abovementioned disadvantages of continuous operation are avoided and the target products are obtained in high yield and with high selectivity.

It has now been found that the conversion of olefins into hydroformylation products in hydroformylation by the single-stage process can be increased if the amount of aqueous cobalt salt solution fed into the reactor is greater than the amount of aqueous phase discharged with the liquid reaction mixture and the gas from the reactor and part of the bottom phase is continuously discharged from the reactor to keep the level of the aqueous bottom phase constant.

The present invention provides a single-stage continuous process for the hydroformylation of olefins having at least 5 carbon atoms to the corresponding aldehydes and/or alcohols having at least 6 carbon atoms in the presence of unmodified cobalt catalysts in a process in which catalyst formation, catalyst extraction and hydroformylation occur in the same reactor in which an aqueous phase and an organic phase are present, which is characterized in that the amount of aqueous cobalt salt solution fed into the reactor is greater than the amount discharged from the reactor as aqueous phase with the liquid reaction mixture and the gas phase and part of the aqueous bottom phase is discharged continuously from the reactor to keep the level of the aqueous bottom phase constant.

Compared to the known single-stage processes, for example that described in DE 196 54 340, the process of the invention has the following advantages: Higher conversions of olefins into hydroformylation products are achieved at the same temperature or the reaction temperature can be decreased at the same conversion, as a result of which the selectivity to the formation of hydroformylation products is increased. Furthermore, it is also possible to hydroformylate olefins which themselves and their hydroformylation products have only a low solvent capability for water by the single-stage process.

The present invention is a single-stage continuous hydroformylation process in which the formation of the active cobalt catalyst from an aqueous cobalt salt solution, extraction of the active catalyst from the aqueous phase into the organic phase and hydroformylation take place simultaneously in the reactor, with the amount of aqueous cobalt salt solution fed into the reactor being more than the amount discharged from the reactor as aqueous phase with the liquid reaction mixture and the excess synthesis gas and the excess of aqueous phase being removed by continuously taking off part of the aqueous bottom phase.

In the process of the invention, from 2 to 99% by mass, in particular from 5 to 80% by mass and very particularly preferably from 10 to 60% by mass, of the water fed into the reactor with the cobalt salt solution is removed by taking off part of the aqueous bottom phase. The proportion of water which is taken off from the reactor with the aqueous bottom phase is dependent mainly on the olefins to be hydroformylated and the hydroformylation temperature.

In a homologous series of aldehydes or alcohols which can be formed in a hydroformylation, the solvent capability for water decreases with increasing molar mass. This has the consequence that as the molar mass of the starting olefins increases, an ever smaller amount of water is transported from the reactor with the liquid reaction mixture, so that an increasing proportion of water has to be removed by taking off part of the aqueous bottom phase from the reactor. The optimal conditions in each case can easily be determined by a person skilled in the art by means of preliminary experiments.

The formation of the active cobalt catalyst is quite slow at temperatures below 160° C. At temperatures above 160° C., in particular above 180° C., on the other hand, the catalyst is formed quickly so that the aqueous solution is depleted in cobalt salts, which limits the formation of the active catalyst. Catalyst formation can be increased by partial replacement of the aqueous bottom phase which is depleted in cobalt compounds by fresh cobalt salt solution.

It is thus advantageous, depending on the starting olefin and the hydroformylation temperature, to remove different proportions of the water fed into the reactor with the aqueous cobalt salt solution by taking off part of the aqueous bottom phase.

For example, in the hydroformylation of a $C_8$-olefin mixture consisting essentially of n-octenes, 3-methylheptenes and 3,4-dimethylhexenes in the temperature range from 180 to 190° C., from 5 to 70% of the water fed into the reactor is removed by discharging part of the bottom phase.

The hydroformylation is carried out in a high-pressure reactor, preferably a cascaded bubble column reactor, into which olefins, an aqueous cobalt salt solution and synthesis gas are introduced, preferably by means of a mixing nozzle.

The level of the aqueous bottom phase in the hydroformylation reactor is kept constant or virtually constant. This means that during steady-state operation under constant reaction conditions the phase boundaries between the lower aqueous phase in which part of the organic phase is dispersed and the organic phase above it is established at a level whose height preferably fluctuates by less than ±5% about a mean. This mean height of the phase boundary can be above or below or at the height of the outlet opening of the mixing nozzle through which the starting materials are introduced into the reactor. The phase boundary can be located from 0 to 1 m, preferably from 0 to 0.5 m and particularly preferably from 0 to 0.2 m, above or below the outlet opening of the mixing nozzle.

The height of the aqueous phase can alter within the limits of the abovementioned range during a change in load. Furthermore, the height of the aqueous phase can alter within these limits as a function of throughput.

The aqueous phase in the lower part of the reactor makes up from 0.5 to 20%, in particular from 1 to 10%, of the liquid present in the reactor.

According to the invention, part of the aqueous bottom phase is discharged from the reactor in the process. This can be carried out periodically or preferably continuously. It preferably occurs at a place at which the bottom phase is subjected to very little movement and thus contains little dispersed organic phase. For example, in a bubble column reactor having a curved bottom, aqueous phase can be taken off from the region of the curved bottom below the introduction nozzle.

In the process of the invention, an aqueous solution of cobalt salts is fed into the hydroformylation reactor. Preference is given to using aqueous solutions of cobalt salts of carboxylic acids, for example cobalt formate or cobalt acetate. It is also possible to use solutions which contain more than one cobalt compound. The cobalt solution is preferably one which is obtained in a particularly preferred embodiment of the overall process, namely in the oxidative removal of cobalt from the hydroformylation product mixture. This solution, which also contains formic acid, can be used directly or after concentration or after reduction of the formic acid content, for example as described in DE 100 09 207.

Solutions whose cobalt salt concentration is greater than 30%, in particular greater than 60%, very particularly preferably greater than 80%, of the saturation concentration of the cobalt salt are preferably used in the process of the invention. If mainly cobalt formate is present in the aqueous solution, the content of cobalt salts, calculated as elemental cobalt, is preferably in the range from 0.7 to 1.7% by mass.

The hydroformylation of the present invention is operated in a manner similar to that described in DE 196 54 340 and DE 101 35 906. The difference is that according to the invention more aqueous cobalt salt solution is introduced and part of the aqueous bottom phase is taken off.

The hydroformylation is carried out in the temperature range from 110 to 250° C., preferably in the temperature range from 130 to 220° C., very particularly preferably in the temperature range from 160° C. to 190° C.

The reaction pressure is in the range from 100 to 400 bar, in particular in the range from 150 to 300 bar. The volume ratio of hydrogen to carbon monoxide in the synthesis gas, namely the mixture of hydrogen and carbon monoxide used, is in the range from 1:2 to 2:1.

In the present invention, the starting olefin or olefin mixture, the aqueous solution containing the cobalt compounds and synthesis gas and, if desired, a solvent are introduced into the bottom of the hydroformylation reactor. The bottom of the reactor contains an aqueous phase in which small amounts of organic phase are dispersed.

To obtain a high reaction rate, it is advantageous to mix the aqueous bottom phase with the organic phase and synthesis gas and also the aqueous cobalt salt solution. The intensive mixing avoids concentration gradients of the reactants. Furthermore, mixing of the aqueous bottom phase with the organic phase promotes transfer of the catalyst formed into the organic phase in which the hydroformylation mainly proceeds.

The mixing of the reaction components (olefin, synthesis gas, aqueous cobalt salt solution) with themselves and/or hydroformylation mixture and also the mixing of the two liquid phases in the reactor can be effected by means of suitable engineering devices.

Olefin, synthesis gas and aqueous cobalt salt solution can be introduced separately, advantageously by means of nozzles, into the reactor. It is also possible for two components to be introduced together through one or more mixing nozzles into the reactor and the third component to be introduced separately. However, it is advantageous to feed all three components together through one or more mixing nozzles into the reactor.

The aqueous bottom phase can be circulated by means of a pump which is installed in a circulation line. Mixing of the aqueous phase and mixing of the aqueous phase with the organic phase and synthesis gas can also be achieved by feeding part of the aqueous phase from the reactor to the mixing nozzle for the starting materials. This can be achieved by means of a pump. Another possibility is to suck part of the aqueous bottom phase from the reactor by means of the fluid flow in the mixing nozzle.

The ejector action of mixing nozzles is influenced by the momentum of the exiting gas and the exiting liquid. High liquid velocities of from 3 to 300 m/s, particularly preferably from 10 to 100 m/s, very particularly preferably from 15 to 70 m/s, at the point or points of mixing are preferred.

The reaction mixture from the hydroformylation reactor contains starting material (olefins), products (aldehydes, alcohols, formic esters), by-products and cobalt carbonyl compounds. The latter can be separated off from the reaction mixture by means of technical measures known per se. The removal of the cobalt carbonyls is preferably carried out oxidatively. For this purpose, the reaction mixture is partially depressurized, in particular to from 10 to 15 bar, and reacted with oxygen-containing gases, in particular air or oxygen, at temperatures of from 90° C. to 160° C. in the presence of an acidic cobalt(II) salt solution in a reactor (cobalt removal unit) and in this way oxidatively freed of cobalt carbonyl compounds. These are decomposed to form cobalt(II) salts. Cobalt removal methods are well known and are comprehensively described in the literature, e.g. in "New Syntheses with Carbon Monoxide", Springer Verlag (1980), Berlin, Heidelberg, New York, page 158 ff. After oxidation, the mixture is separated into the organic product phase, offgas and process water. The process water separated off typically has a pH of from 1.5 to 4.5 and a cobalt content of from 0.5 to 2% by mass. The major part of the process water is recirculated to the cobalt removal unit, if appropriate with addition of water. The other part is preferably recirculated to the hydroformylation reactor.

The aqueous bottom phase taken off from the hydroformylation reactor contains cobalt(II) salts and also organic substances and cobalt carbonyl compounds. If this solution cannot be used as such, it is advantageous to introduce it together with the hydroformylation mixture into the cobalt removal unit.

The aqueous phase taken off at the bottom can, before it is used further or worked up, preferably be extracted with starting olefin so that part of the cobalt carbonyls and the organic substances present therein is taken up by the olefin phase. The olefin phase laden with cobalt carbonyls is fed to the hydroformylation reactor. The extraction is preferably carried out in countercurrent in customary industrial extraction apparatuses, for example in a packed column. The extraction temperature can be in the range from 20 to 220° C. The pressure in the reaction column can be from 1 to 400 bar.

The organic reaction mixture obtained after removal of the cobalt carbonyls is worked up by known methods. For example, it can be separated by distillation into a hydrocarbon fraction (which may contain unreacted olefins), aldehydes, other products of value, and further substances. The hydrocarbon fraction containing unreacted olefins can be partly recirculated to the same hydroformylation step according to the invention or to a further hydroformylation step which can also be operated according to the invention. The aldehydes obtained can be utilised as such or can be used as starting material for the preparation of other materials, for example carboxylic acids, amines, nitriles or aldol condensation products. Furthermore, the hydroformylation mixture can be hydrogenated before or after removal of the unreacted olefins to form the corresponding primary alcohols which can be used, inter alia, as precursors for plasticisers or detergents.

As starting materials for the process of the invention, it is in principle possible to use all olefins having at least 5 carbon atoms. The starting materials used can be linear or branched α-olefins, linear or branched olefins having internal double bonds, cycloaliphatic olefins or olefins having aromatic groups. It is possible to use materials having one or more olefinic double bond(s). Preference is given to using olefins or olefin mixtures having from 6 to 24 carbon atoms. The mixtures can comprise olefins having the same number of carbon atoms, similar (+2) numbers of carbon atoms or significantly different (>+2) numbers of carbon atoms. As olefins which can be used as starting material either in pure form, in an isomer mixture or in a mixture with further olefins, mention may be made by way of example of: 1-, 2- or 3-hexene, 1-heptene, linear heptenes having an internal double bond (2-heptene, 3-heptene, etc.), mixtures of linear heptenes, 2- or 3-methyl-1-hexene, 1-octene, linear octenes having an internal double bond, mixtures of linear octenes, 2- or 3-methylheptene, 1-nonene, linear nonenes having an internal double bond, mixtures of linear nonenes, 2-, 3- or 4-methyloctenes, 1-, 2-, 3-, 4- or 5-decene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecenes having an internal double bond, mixtures of linear hexadecenes. Further suitable starting materials are, inter alia, the mixture of isomeric hexenes obtained in the dimerization of propene (dipropene), the mixture of isomeric octenes obtained in the dimerization of butenes (dibutene), the mixture of isomeric nonenes obtained in the trimerization of propene (tripropene), the mixture of isomeric dodecenes obtained in the tetramerization of propene or the trimerization of butenes (tetrapropene or tributene), the hexadecene mixture obtained in the tetramerization of butenes (tetrabutene) and olefin mixtures prepared by cooligomerization of olefins having different numbers of carbon atoms (preferably from 2 to 4), if desired after separation into fractions having the same number of carbon atoms or similar (±2) numbers of carbon atoms by distillation. Furthermore, it is possible to use olefins or olefin mixtures which have been produced by the Fischer-Tropsch synthesis. Olefins which have been prepared by olefin metathesis or by other industrial processes can also be used. Preferred starting materials are mixtures of isomeric octenes, nonenes, dodecenes or hexadecenes, i.e. oligomers of lower olefins such as n-butenes, isobutene or propene. Further well-suited starting materials are oligomers of $C_5$ olefins.

In addition, the process of the invention is also suitable for the hydroformylation of polymeric olefins, for example polyisobutene, polybutadiene, 1,3-butadiene-isobutene or butene copolymers having a molar mass up to 6000 dalton, if desired using a diluent.

When $C_8$-, $C_{12}$- or $C_{16}$-olefin mixtures are the starting materials, particular preference is given to using ones which have been prepared by oligomerization of linear butenes over fixed-bed nickel catalysts, for example by the Octol process (Hydrocarbon Process, Int. Ed. (1986) 65 (2. Sect. 1) pages 31-33).

Figure 2:
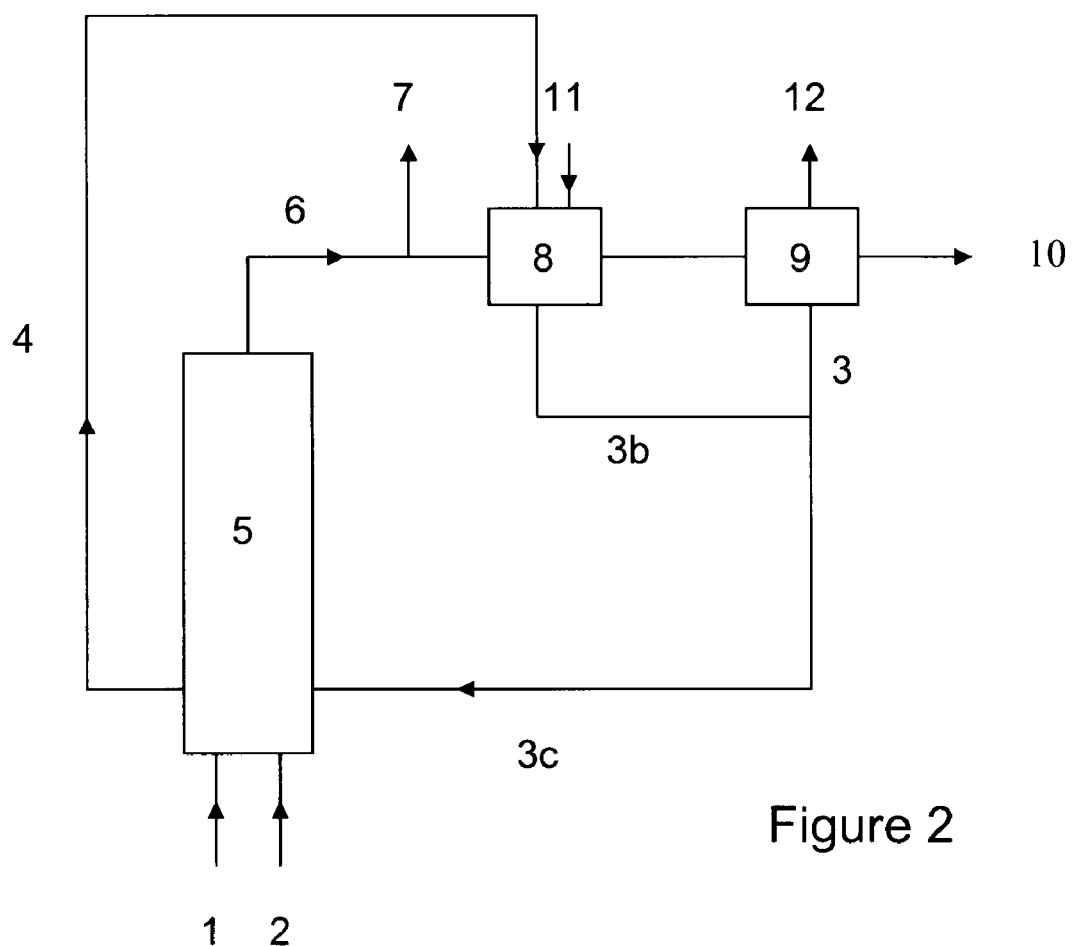

The invention is illustrated with the aid of FIGS. 1 and 2. Self-evident plant details which are not necessary for an understanding of the invention have been left out in the interests of clarity.

FIG. 1 schematically shows the simplest type of plant for carrying out the process of the invention. This plant does not have a closed catalyst circuit. Starting olefin (1), synthesis gas (2) and aqueous cobalt(II) salt solution (3) are fed into the hydroformylation reactor (5) in which an aqueous bottom phase is present. A part (4) of the aqueous bottom phase is taken off. The hydroformylation mixture (6) is, if desired after taking off excess synthesis gas (7), fed to a cobalt removal unit (8/9). A stream (3a) containing cobalt compounds is separated off and a virtually cobalt-free hydroformylation mixture (10) is obtained.

FIG. 2 schematically shows a plant in which a preferred embodiment of the process of the invention can be carried out. Olefin (1), synthesis gas (2) and an aqueous cobalt salt solution (3c) are fed into the hydroformylation reactor (5) in which an aqueous bottom phase is present. A part (4) of the aqueous bottom phase is taken off. The output (6) from the hydroformylation reactor (5) is partially depressurized and a part (7) of the excess synthesis gas is separated off. In the oxidizer (8), the partially depressurized hydroformylation mixture (6) together with the bottom offtake stream (4) is reacted with an oxygen-containing gas (11) in the presence of the process water (3b), resulting in cobalt carbonyls being oxidized to cobalt(II) salts. The resulting mixture is separated into offgas (12), hydroformylation mixture (10) and process water (3) in the separation vessel (9). A part (3b) of the process water is recirculated to the oxidizer (8) and the other part (3c) is recirculated to the hydroformylation reactor (5). The hydroformylation mixture (10) is worked up by known methods. The amount of water and the traces of cobalt which are discharged with the stream (10) are replaced, for example by introduction of the corresponding amounts into the vessel (9).

Figure 3:
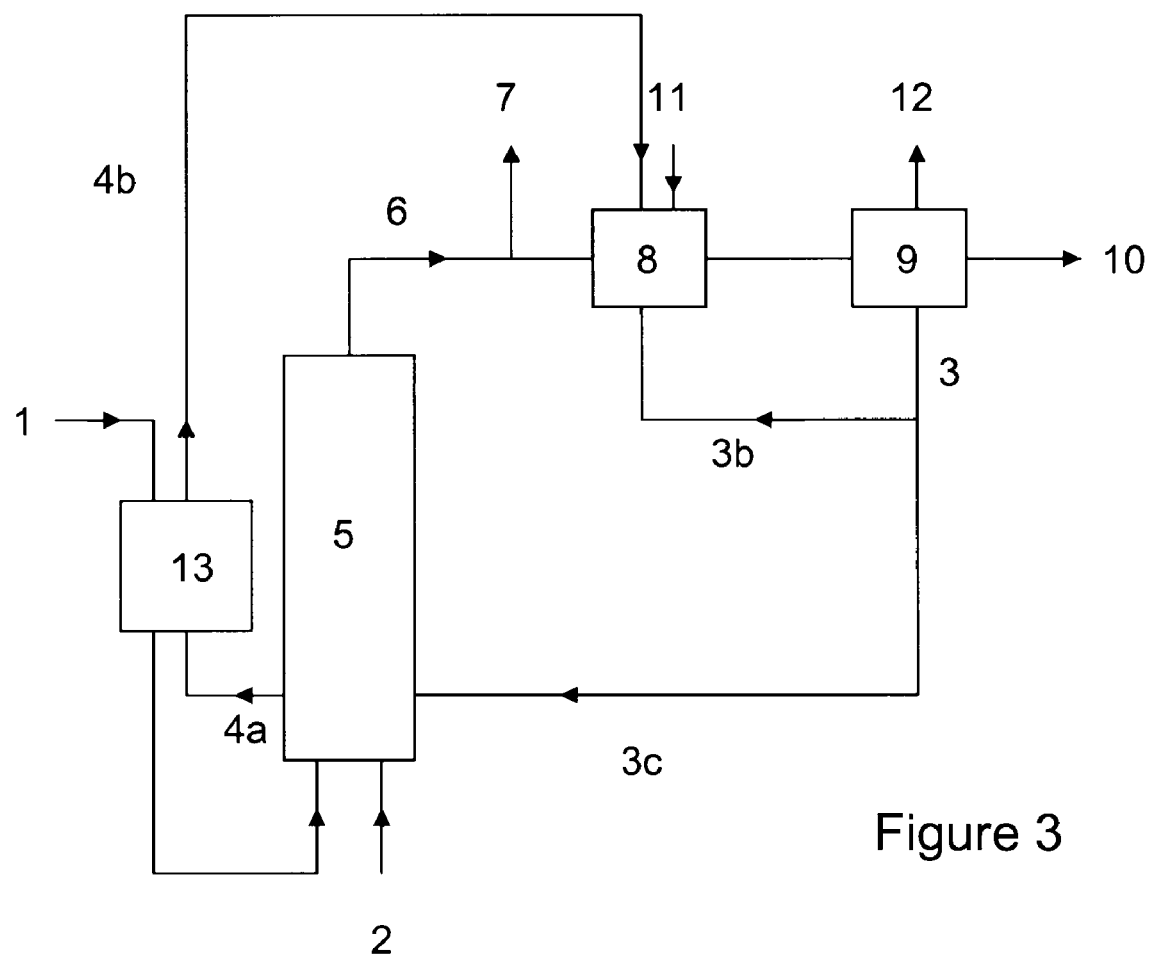

FIG. 3 shows a further embodiment of the process of the invention. This embodiment differs from the variant shown in FIG. 2 in that the aqueous bottom phase (4a) taken off from the reactor is extracted with starting olefin (1) in the extractor (13).

The following examples illustrate the invention without restricting it thereto.

EXAMPLE 1

Hydroformylation of $C_8$-olefins without Discharge of Cobalt Water (not According to the Invention)

The continuous hydroformylation of the $C_8$-olefin mixture was carried out using an experimental plant which consisted essentially of a vertical high-pressure tube reactor (90 mm internal diameter; length=3600 mm) and a downstream cobalt removal vessel (20 l capacity) filled with Raschig rings and also a phase separation vessel. The reaction space of the high-pressure reactor was cascaded by means of five perforated plates installed orthogonally to the flow direction. A three-fluid mixing nozzle was used for introduction of the starting materials olefin mixture, synthesis gas and aqueous catalyst solution. The contents of the reactor could be heated or cooled as required by means of installed heating and cooling facilities.

The formation of the active cobalt catalyst, the extraction of the active cobalt catalyst into the olefin phase and the hydroformylation proceeded simultaneously in the high-pressure reactor.

As $C_8$-olefin mixture, use was made of a di-n-butene mixture prepared by the Octol process of Oxeno GmbH.

The reactor was filled with dibutene and brought to the reaction temperature of 180° C. Dibutene, aqueous cobalt acetate solution containing 1% by mass of cobalt, calculated as element, and synthesis gas having a $CO/H_2$ volume ratio of 1:1 were subsequently fed continuously into the bottom of the reactor via the mixing nozzle.

The following throughputs were set: 5.0 kg/h of dibutene and 0.35 kg/h of cobalt acetate solution. The reactor was regulated by means of synthesis gas to a constant reaction pressure of 280 bar at a synthesis gas throughput of 2.5-3.5 standard m³/h.

The hydroformylation mixture was taken off continuously at the top of the reactor and depressurized to 15 bar in the cobalt removal stage.

An aqueous bottom phase was formed in the lower part of the reactor and the level of this remained unchanged after reaching pseudo-steady-state equilibrium. To achieve this, water and cobalt were introduced into the reactor in an amount corresponding to that removed from the reactor with the liquid hydroformylation mixture and excess synthesis gas.

In the cobalt removal stage, the hydroformylation mixture was freed of active cobalt catalyst by oxidation of the cobalt carbonyl complexes by means of air in the presence of acidic cobalt salt solution. The two phases were subsequently separated in the downstream separation vessel.

The cobalt-free reaction product after 24 hours of operation had, according to GC analysis, the following composition in % by mass: 5.1 of $C_8$-olefins, 3.1 of $C_8$-paraffins, 29.9 of isononanals, 53.8 of isononanols, 3.9 of esters (nonyl formates) and 4.2 of high boiling fractions. This corresponds to a dibutene conversion of 93.5% and a selectivity to desired products of 91.2%. (Desired products are isononanals, isononanols and nonyl formates.)

EXAMPLE 2

Hydroformylation of Dibutene with Discharge of Cobalt Water (According to the Invention)

The experiment described in Example 1 was continued with the throughput of cobalt acetate solution being increased from 0.35 kg/h to 0.50 kg/h. All other conditions were kept constant. To keep the level of aqueous phase constant, too, 0.15 kg/h of process water had to be taken off from the reactor after reaching the pseudo-steady state and this process water was fed to the cobalt removal unit.

The cobalt-free reaction mixture after 24 h had, according to GC analysis, the following composition in % by mass: 4.4 of $C_8$-olefins, 2.7 of $C_8$-paraffins, 30.7 of isononanals, 54.1 of isononanols, 4.0 of esters (isononyl formates) and 4.1 of high boiling fractions. This corresponds to a dibutene conversion of 94.5% and a selectivity to desired products of 92.0%.

It can be seen that both the dibutene conversion and the selectivity to desired products are increased by means of the measure according to the invention.

The invention claimed is:
1. A single-stage continuous process for hydroformylation of an olefin having at least 5 carbon atoms to at least one of a corresponding aldehyde and a corresponding alcohol having at least 6 carbon atoms in the presence of one or more unmodified cobalt catalysts, wherein: catalyst formation, catalyst extraction and hydroformylation occur in a same reactor in which an aqueous phase and an organic phase are present;
an amount of aqueous cobalt salt solution fed into the reactor is greater than the amount discharged from the reactor as aqueous phase with a liquid reaction mixture and a gas phase; and part of an aqueous bottom phase is discharged continuously from the reactor to keep a level of the aqueous bottom phase constant.
2. The process according to claim 1, wherein
from 2 to 99% by mass of the water fed into the reactor is removed by taking off part of the aqueous bottom phase.
3. The process according to claim 1, wherein
from 5 to 80% by mass of the water fed into the reactor is removed by taking off part of the aqueous bottom phase.
4. The process according to claim 1, wherein
from 10 to 60% by mass of the water fed into the reactor is removed by taking off part of the aqueous bottom phase.
5. The process according to claim 1, wherein
the level of the aqueous bottom phase in the hydroformylation reactor is kept constant or virtually constant, with a phase boundary between the lower aqueous phase and an organic phase above the lower aqueous phase during steady-state operation under constant reaction conditions being at a level whose height fluctuates by less than ±5% with respect to a mean.
6. The process according to claim 5, wherein
an mean height of the phase boundary is at the height of the outlet opening of a mixing nozzle through which starting materials are introduced into the reactor.
7. The process according to claim 6, wherein
the phase boundary is located from 0 to 1 m, above or below the outlet opening of a mixing nozzle.
8. The process according to claim 1, wherein
the bottom phase taken off is extracted with starting olefin.
9. The process according to claim 1, wherein
the aqueous cobalt salt solution fed into the reactor essentially consists of cobalt formates.
10. The process according to claim 1, wherein
a concentration of cobalt salts in the aqueous solution fed into the reactor is greater than 30%, of a saturation concentration.
11. The process according to claim 1, wherein
the olefin comprises an olefin mixture having from 6 to 24 carbon atoms.
12. The process according to claim 11, wherein
the olefin comprises an olefin mixture having 8 or 12 or 16 carbon atoms.
13. The process according to claim 11, wherein
the olefin comprises an olefin mixture prepared by oligomerization of linear butenes over fixed-bed nickel catalysts.

* * * * *